United States Patent
Ma

(10) Patent No.: US 11,006,963 B2
(45) Date of Patent: May 18, 2021

(54) DETACHMENT MECHANISMS FOR IMPLANTABLE DEVICES

(71) Applicant: Jianlu Ma, Irvine, CA (US)

(72) Inventor: Jianlu Ma, Irvine, CA (US)

(*) Notice: Subject to any disclaimer, the term of this patent is extended or adjusted under 35 U.S.C. 154(b) by 1000 days.

(21) Appl. No.: 14/475,047

(22) Filed: Sep. 2, 2014

(65) Prior Publication Data

US 2015/0066073 A1    Mar. 5, 2015

Related U.S. Application Data

(60) Provisional application No. 61/872,861, filed on Sep. 3, 2013.

(51) Int. Cl.
    *A61B 17/12* (2006.01)
(52) U.S. Cl.
    CPC .... *A61B 17/12113* (2013.01); *A61B 17/1214* (2013.01); *A61B 2017/12063* (2013.01)
(58) Field of Classification Search
    CPC ..................... A61B 17/1214; A61B 17/12113
    USPC ........ 606/108, 191, 194, 200; 623/1.11–1.54
    See application file for complete search history.

(56) References Cited

U.S. PATENT DOCUMENTS

| | | |
|---|---|---|
| 4,735,201 A | 4/1988 | O'Reilly |
| 4,994,069 A | 2/1991 | Ritchart et al. |
| 5,108,407 A | 4/1992 | Geremia et al. |
| 5,122,136 A | 6/1992 | Guglielmi et al. |
| 5,354,295 A | 10/1994 | Guglielmi et al. |
| 5,423,829 A | 6/1995 | Pham et al. |
| 5,624,449 A | 4/1997 | Pham et al. |
| 5,749,894 A | 5/1998 | Engelson |
| 5,759,161 A | 6/1998 | Ogawa et al. |
| 5,846,210 A | 12/1998 | Ogawa et al. |
| 5,944,733 A | 8/1999 | Engelson |
| 5,976,131 A | 11/1999 | Guglielmi et al. |
| 6,077,260 A | 6/2000 | Wheelock |
| 6,346,091 B1 | 2/2002 | Jacobsen et al. |
| 6,409,721 B1 | 6/2002 | Wheelock et al. |
| 6,425,893 B1 | 7/2002 | Guglielmi |
| 6,589,236 B2 | 7/2003 | Wheelock et al. |

(Continued)

FOREIGN PATENT DOCUMENTS

| | | |
|---|---|---|
| EP | 2104521 B1 | 9/2009 |
| WO | 2007/071436 A2 | 6/2007 |

(Continued)

OTHER PUBLICATIONS

European Supplemental Search Report dated Apr. 12, 2007 for EP Application No. 14841701.7.

(Continued)

*Primary Examiner* — Sarah W Aleman
(74) *Attorney, Agent, or Firm* — Raymond Sun

(57) ABSTRACT

The present invention relates to detachment mechanisms for delivering and releasing implantable devices into a body lumen. According to certain aspects, systems of the invention include a junction that couples an implantable device to a delivery member. The junction includes an anodic portion and a cathodic portion galvanically coupled to the anodic portion such that the anodic portion corrodes when exposed to an electrolytic fluid, thereby detaching the implantable device from the delivery member without application of energy from an external power source.

7 Claims, 10 Drawing Sheets

(56) References Cited

U.S. PATENT DOCUMENTS

| | | |
|---|---|---|
| 6,620,152 B2 | 9/2003 | Guglielmi |
| 6,623,493 B2 | 9/2003 | Wallace et al. |
| 6,716,238 B2 | 4/2004 | Elliott |
| 6,743,251 B1 | 6/2004 | Eder |
| 7,323,000 B2 | 1/2008 | Monstdt et al. |
| 7,905,902 B2 | 3/2011 | Huitema et al. |
| 8,016,853 B2 | 9/2011 | Griffen et al. |
| 8,377,112 B2 | 2/2013 | Griffin et al. |
| 8,556,927 B2 | 10/2013 | Dehnad |
| 2002/0111646 A1* | 8/2002 | Gifford, III ...... A61B 17/12022 606/195 |
| 2002/0133189 A1* | 9/2002 | Gifford, III ...... A61B 17/12022 606/191 |
| 2003/0176857 A1* | 9/2003 | Lee .................. A61B 17/12022 606/32 |
| 2004/0002752 A1 | 1/2004 | Griffin et al. |
| 2004/0078050 A1* | 4/2004 | Monstadt ......... A61B 17/12022 606/191 |
| 2006/0079927 A1 | 4/2006 | Kaemmerer et al. |
| 2006/0282112 A1 | 12/2006 | Griffin |
| 2007/0073334 A1* | 3/2007 | Ramzipoor ...... A61B 17/12145 606/200 |
| 2007/0213813 A1* | 9/2007 | Von Segesser ....... A61F 2/2418 623/2.18 |
| 2007/0270942 A1 | 11/2007 | Thomas |
| 2008/0161906 A1 | 7/2008 | Atanasoska et al. |
| 2008/0287982 A1 | 11/2008 | Harreld |
| 2009/0002752 A1 | 1/2009 | Sugiyama |
| 2009/0138036 A1* | 5/2009 | Nardone .......... A61B 17/12022 606/200 |
| 2009/0171432 A1 | 7/2009 | Von Segesser et al. |
| 2009/0254111 A1* | 10/2009 | Monstadt ......... A61B 17/12022 606/191 |
| 2009/0270901 A1* | 10/2009 | Kelleher .......... A61B 17/12022 606/191 |
| 2011/0238148 A1* | 9/2011 | Monstadt ......... A61B 17/12022 623/1.11 |
| 2013/0331883 A1 | 12/2013 | Strauss et al. |
| 2014/0018844 A1 | 1/2014 | Dehnad |
| 2014/0039535 A1* | 2/2014 | Eskuri ............. A61B 17/12022 606/191 |

FOREIGN PATENT DOCUMENTS

| | | |
|---|---|---|
| WO | 2007/136965 A1 | 11/2007 |
| WO | 2007/139668 A3 | 12/2007 |

OTHER PUBLICATIONS

International Search Report and Written Opinion dated Dec. 3, 2014, for International Patent Application No. PCT/US2014/053722, filed Sep. 2, 2014, (14 pages).

Internaional Preliminary Report on Patentabiliy for PCT/US2014/053722.

* cited by examiner

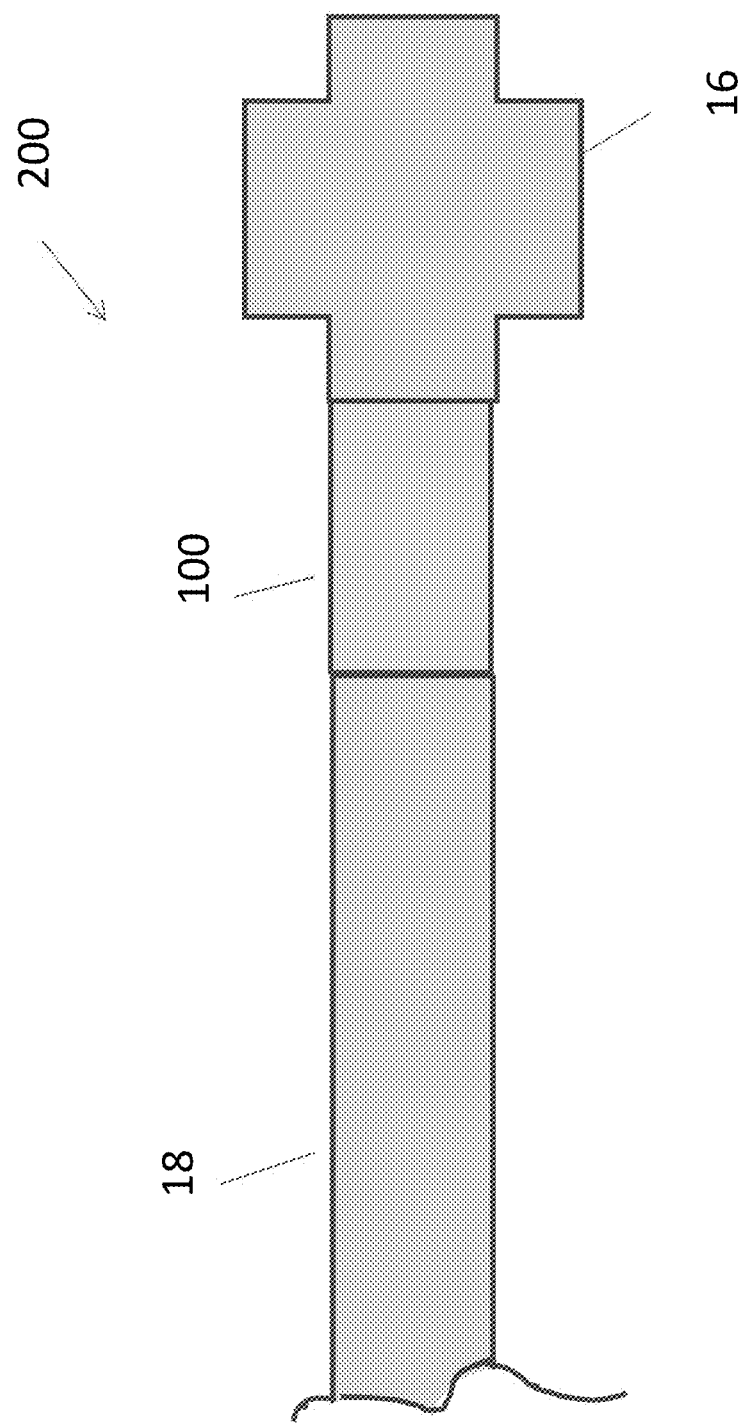

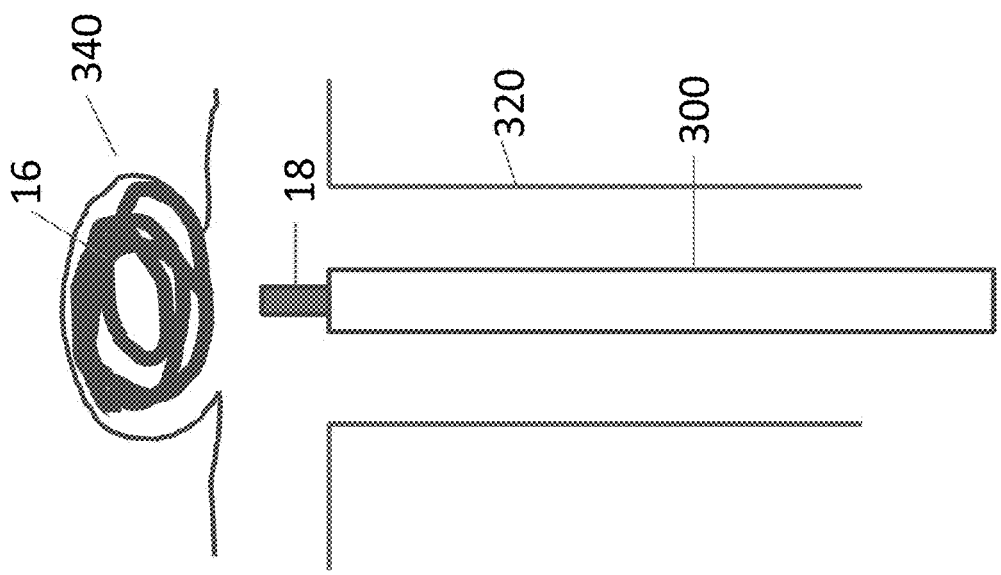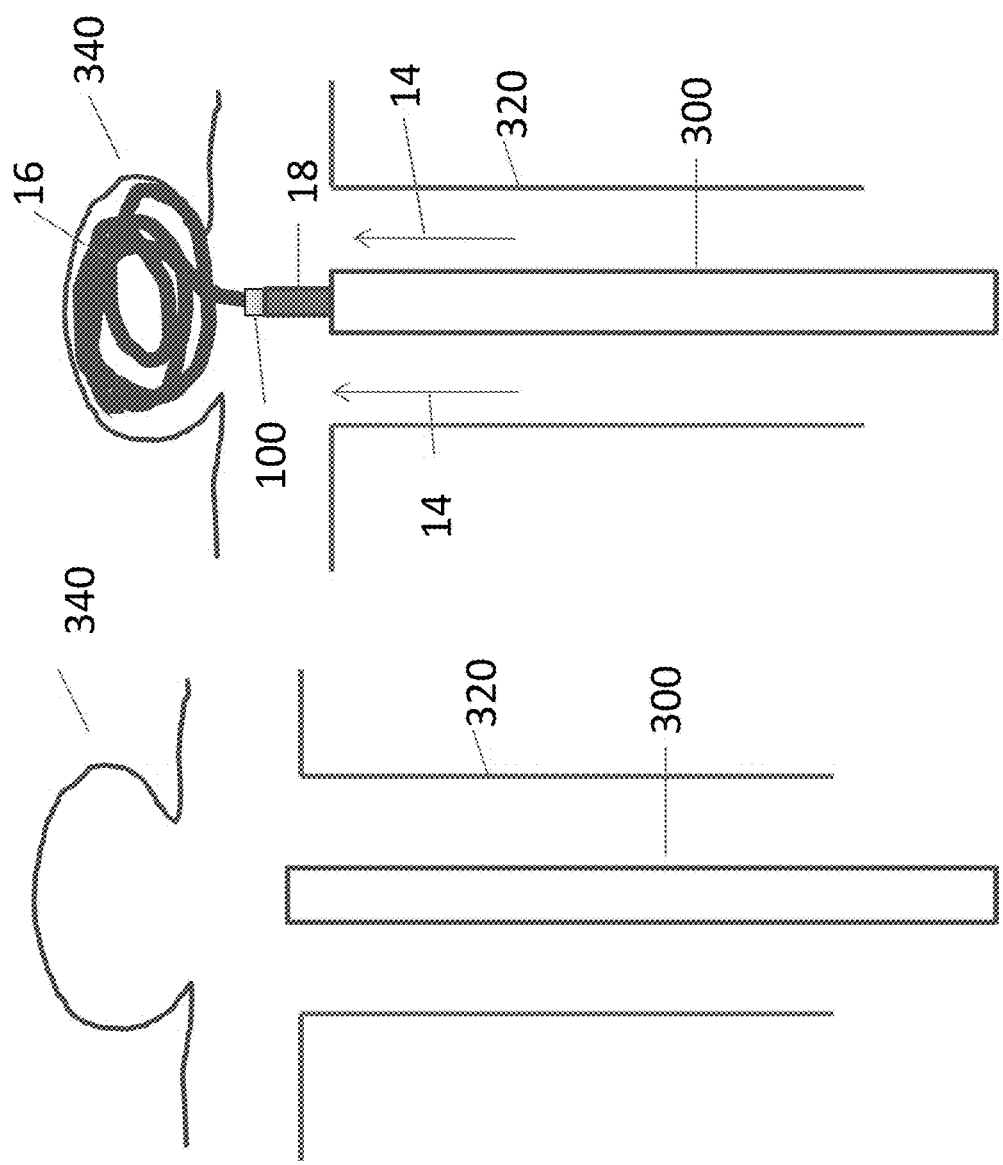

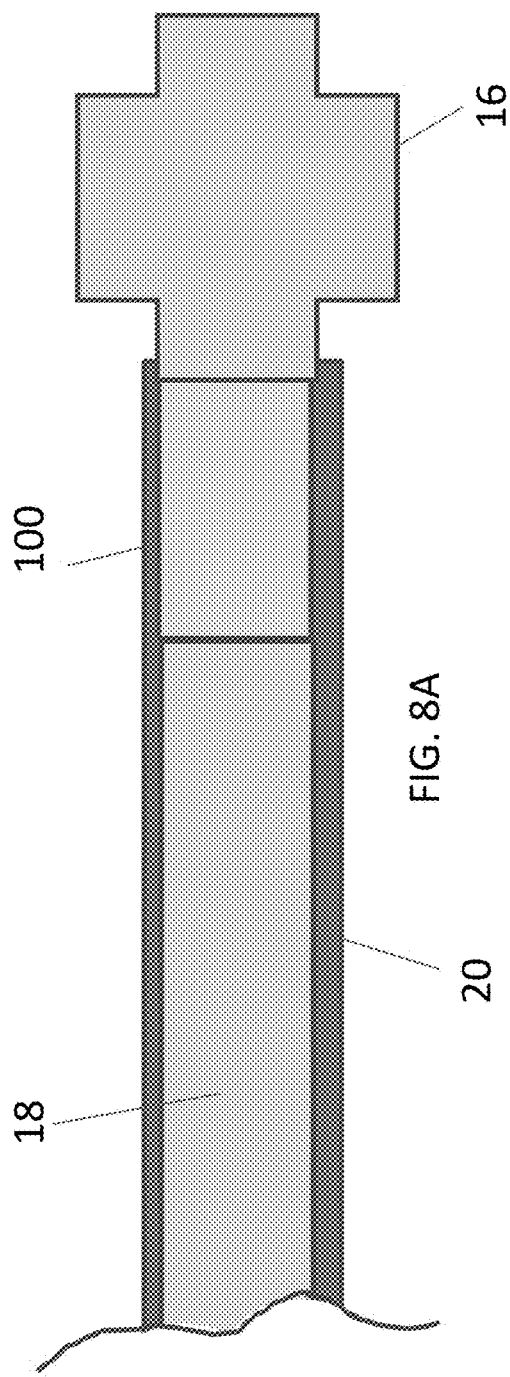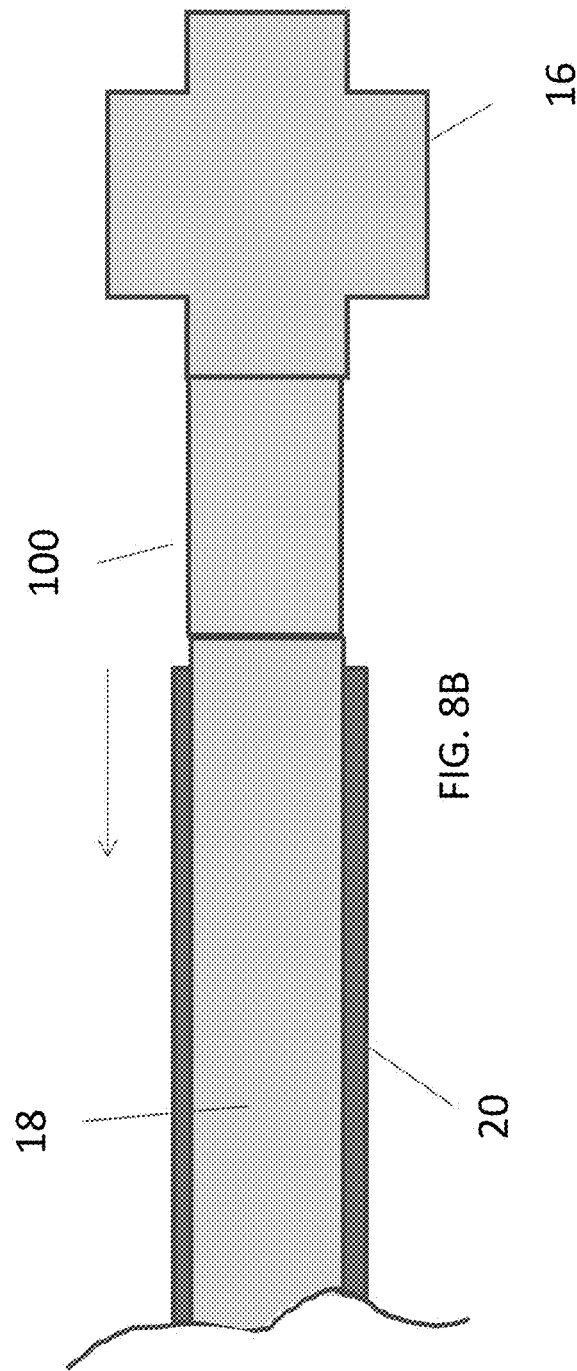

DETACHMENT MECHANISMS FOR IMPLANTABLE DEVICES

CROSS REFERENCE TO RELATED APPLICATIONS

This application claims the benefit of and priority to U.S. Patent Provisional Application No. 61/872,861 filed on Sep. 3, 2013, the entirety of which is incorporated by reference herein.

TECHNICAL FIELD

The present invention relates to detachment mechanisms for delivering and releasing implantable devices into a body lumen.

BACKGROUND OF THE INVENTION

An aneurysm is a sac or balloon-like bulge formed in the wall of a blood vessel. Typically, aneurysms are formed in arteries, the blood vessels that carry oxygen-rich blood from the heart throughout the body and its organs. Formation of aneurysms occur when arteries are unable to withstand the pressure of normal blood flow due to weakened or injured arterial walls, e.g. caused by cardiovascular disease, genetic conditions, and trauma. When an aneurysm grows large, it may rupture or dissect. Rupture causes internal bleeding through the aneurysm into the body, and dissection splits the tissue layers forming the artery and causes bleeding among the layers of the arterial wall.

Most aneurysms occur in the aorta, a vessel running through chest and abdomen, but aneurysms also occur in the brain. Aortic and cerebral aneurysms if allowed to rupture/dissect can cause serious complications and are often fatal, particularly aortic aneurysms which have about 10-25% post-rupture survival rate. Ruptured cerebral aneurysms are frequently associated with hemorrhagic stroke and permanent nerve damage.

Early diagnosis and intervention can help prevent rupture and dissection. While medicinal treatment (i.e. blood pressure medicines) is successful for some aneurysms, surgery is the preferred treatment method. Surgical intervention may involve occluding the vessel upstream from the aneurysm or occluding the aneurysm itself.

There are a variety of vaso-occlusion implants that can be delivered and implanted to occlude the vessel or aneurysm, e.g., microcoils, stents, cages. In order to deliver the vaso-occlusion implant, the implant is usually attached to a wire or other push rod by a sacrificial joint and driven up the artery to the target occlusion site. Once positioned at the target occlusion site, the implant is detached from the wire either by applying energy (i.e. electrical current, radiofrequency energy, heat, laser, etc.) from an external source to sever the sacrificial joint, or by mechanical detachment approach.

There are several drawbacks to using an external energy source to sever the sacrificial joint and detach the vaso-occlusion device. The first drawback is the need for an external energy source itself. The vessel at the location of the aneurysm is already weakened, and the application of external laser, radiofrequency, and electrical energy/current can further weaken or damage the vessel. In addition, the external energy may cause thrombi to form within the bloodstream. Also, external energy sources are unreliable in their ability to timely sever the joint and often require a long period of time and/or multiple detachment efforts. Inconsistent or lengthy detachment events are undesirable because most procedures are conducted under general anesthesia, where time is of the essence. Finally, incomplete or false detachment caused by external energy sources often disrupt the positioning of the vaso-occlusion device at its target implantation site, resulting in inaccurate placement of the device and in some instances a failed procedure.

SUMMARY OF THE INVENTION

The present invention provides systems and related methods for delivering and detaching an implantable device into one's intravascular system without application of energy/current from an external source. Systems of the invention rely on galvanic corrosion, without external energy, in order to rapidly detach an implantable device from a delivery member. Systems of the invention include a junction that connects the implant to the delivery member and is formed from an anodic metal in contact with a cathodic metal. The galvanic nature of the metals causes the anodic metal to degrade upon exposure to an electrolytic fluid (electrolyte). The degradation of the anodic material detaches the implant at the target implantation site, and allows easy withdrawal of the delivery member from the intravascular.

According to certain aspects, systems of the invention include a junction that couples delivery member to an implant. The delivery member may be a push wire or micro-catheter, and is designed to fit within a body lumen. The attached implant may be driven through a body lumen by the delivery member to a target implantation site. At the target implantation site, the implant may be detached from the delivery member via the junction. For detachment, the junction is exposed to an electrolytic fluid, such as blood, and/or other body fluids, that causes an anodic portion of the junction to corrode without application of energy from an external power source. In order to create a faster or more controlled detachment, other more conductive electrolytic fluid may be introduced in to the body lumen at or near the implantation site from an external fluid source. For example, the electrolytic fluid, such as saline solution and other conductive fluid, may be introduced via a lumen of the delivery member or via a separate fluid delivery catheter. In certain embodiments, the delivery member is disposed within a sheath that initially covers the junction, and, when corrosion is desirable, the sheath is pulled back to expose the junction to electrolytic fluid. Once dissolved/corroded, the implant is detached from the delivery member at the target implantation site, and the delivery member can be removed.

Generally, junctions of the invention include at least one cathodic portion and at least one anodic portion galvanically connected to the cathodic portion. Preferably, the cathodic and anodic portions are in direct contact with each other. The cathodic portion is formed from a metal or alloy that is less galvanically active than a metal or alloy of the anodic portion. In certain embodiments, the cathodic portion is formed from platinum, platinum alloys, platinum-iridium alloys, tantalum, stainless steel, nickel-titanium alloys, cobalt-chromium alloys and combinations thereof. In certain embodiments, the anodic portion is a metallic material formed from magnesium and magnesium alloys. The cathodic and anodic portions may be, for example, a tubular structure, a rod structure, or a thin film or layer. In certain embodiments, the cathodic portion is a tubular structure and the anodic portion is a thin film or layer.

The cathodic and anodic portions of the junction may be arranged, for example, in one or more of the following configurations. In some embodiments, the junction may include at least one cathodic portion that, when the junction couples the implantable device to the delivery device, overlaps with the anodic portion, a distal portion of the delivery member, a proximal portion of the implant, and combinations thereof. In certain embodiments, the junction includes two separate cathodic portions, and the first cathodic portion is operably associated to the proximal portion of the implant and the second cathodic portion is operable associated with a distal portion of a delivery member. In such aspect, the anodic portion of the junction may be flanked by the first and second cathodic portions. In additional embodiments, the anodic portion may be operably coupled to a distal portion of the delivery member, a proximal portion of the implant, or both.

Suitable electrolytic fluids used to galvanic corrode the junction include, for example, blood, plasma, or other biocompatible electrolytic fluid, such as saline. For controlled corrosion, it may be desirable to delay or inhibit exposing the electrolytic fluid to the junction. Accordingly, certain embodiments of the invention include use of a pull-back sheath, a permeable/perforated membrane, or a dissolvable coating in order to delay or inhibit exposure of the electrolytic fluid to junction as desired.

Systems and methods of the invention are suitable for delivering and detaching implants into body lumen. In particular embodiments, the body lumen is a blood vessel within the cardiovascular and cerebrovascular systems. Suitable implants for delivery in accordance with the invention include, for example, coils, stents, cages, etc.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used.

Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar throughout this specification may, but do not necessarily, all refer to the same embodiment.

Furthermore, the described features, structures, or characteristics of the invention may be combined in any suitable manner in one or more embodiments. In the following description, numerous specific details are provided to provide a thorough understanding of embodiments of the invention. One skilled in the relevant art will recognize, however, that the invention may be practiced without one or more of the specific details, or with other methods, components, materials, and so forth. In other instances, well-known structures, materials, and so forth. In other instances, well-known structures, materials, or operations are not shown or described in detail to avoid obscuring aspects of the invention.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

BRIEF DESCRIPTION OF THE DRAWINGS

FIG. 2 generally illustrates a system of the invention with a junction 100 that utilizes the conditions 50 as set forth in FIG. 1.

FIGS. 3A-3C illustrate a system of the invention being used to delivery and detach an implant in to an aneurysm sac.

FIGS. 8A and 8B illustrate use of a pull-back sheath to delay exposure of the junction to an electrolytic fluid.

DETAILED DESCRIPTION OF THE INVENTION

Figure 1:
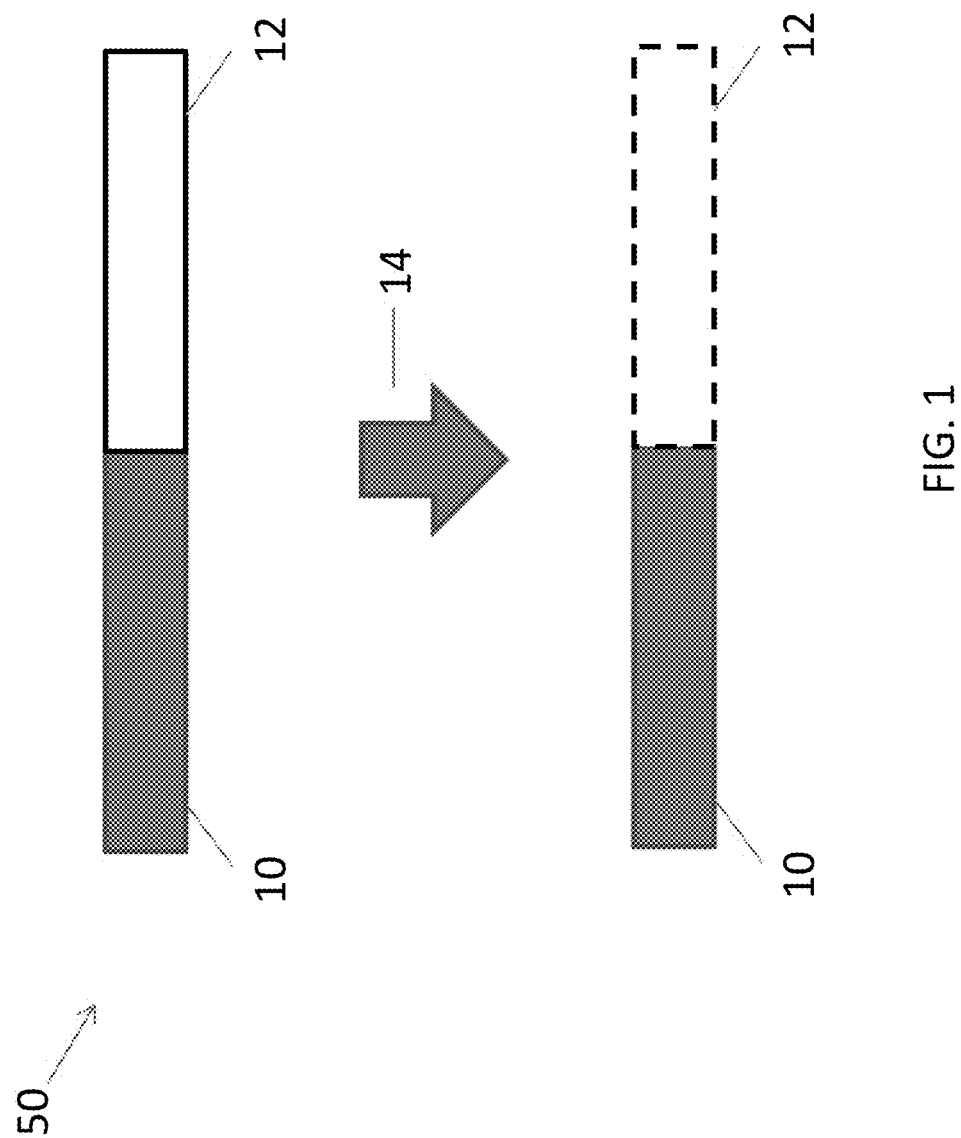
FIG. 1 depicts generally the conditions 50 required for galvanic corrosion to occur.

The present invention provides systems and related methods for detaching an implantable device from a delivery member without application of an external energy source. Aspects of the invention are accomplished by using a junction that decouples an implant from a delivery device based on galvanic corrosion. According to certain embodiments, the junction includes an anodic metal coupled to a cathodic metal such that the anodic metal galvanically corrodes when the junction is exposed to an electrolytic fluid. The degradation of the anodic metal causes the implant to detach at target implantation site and allows unhindered removal of the delivery device from the body lumen. A benefit of the present invention is that the corrosion of the junction and detachment of the implant occur without application energy from an external energy source. Aspects of the systems and methods of the invention, including galvanically-corrodible junctions, delivery devices, and implants, are described in more detail hereinafter.

Systems and methods of the invention deliver an implant within a body lumen. Various lumens of biological structures may receive an implant in accordance with the invention. Those body lumens may include, but not limited to, blood vessels, vasculature of the lymphatic and nervous systems, various structures of the gastrointestinal tract including lumen of the small intestine, large intestine, stomach, esophagus, colon, pancreatic duct, bile duct, hepatic duct, lumen of the reproductive tract including the vas deferens, uterus and fallopian tubes, structures of the urinary tract including urinary collecting ducts, renal tubules, ureter, and bladder, and structures of the head and neck and pulmonary system including sinuses, parotid, trachea, bronchi, and lungs.

Systems and methods of the invention may be used to delivery any suitable implantation device (i.e. implant) into a body lumen. Implants delivered by systems of the invention may be used to, for example: occlude a body lumen; occlude a defect present in a body lumen, such as an aneurysm sac in a vessel; add supplementary framework or stability to a weakened or diseased vessel; repair or replace a valve; and monitor or control physiological conditions within body lumen. Suitable implants include, for example, stents, plugs, coils (e.g., embolic coils), cages, braided or woven implants, sponges, physiological sensor (e.g., temperature, pressure, flow, and/or pH monitor), a filter, or a valve. The implants may be formed from a variety of materials including metallic and/or polymeric materials, e.g. nitinol; stainless steel; Co—Cr alloys; polymers; Pt; Pt alloys; and Ta Alloys. Ideally, the implant is formed from a material that is less active than the anodic portion of the junction. In certain embodiments, the implant is formed from a material that is less active than both the anodic and cathodic portions of the junction.

Systems and methods of the invention are particularly well-suited to deliver stents and coils used in the treatment of intravascular defects. The intravascular defects may be present in the cardiovascular or cerebrovascular systems. The defects may range from aneurysms to weakened vessels due to the presence of atherosclerosis. For aneurysms, treatment typically involves implantation of a vaso-occlusive device into the sac of the aneurysm to block blood flow into the aneurysm or implantation of a vaso-occlusive device into the vessel upstream from the aneurysm to block blood flow into the diseased area of the vessel. Additionally, a stent or tube implant may be delivered into the vessel to form a new vessel path extending past the aneurysm. The stent or tube allows blood to flow through the new vessel path while blocking the aneurysm.

Delivery systems of the invention may optionally involve the introduction of an introducer sheath. Introducer sheaths are known in the art. Introducer sheaths are advanced over the guidewire into the vessel. A catheter or other device, such as the delivery device, may then be advanced through a lumen of the introducer sheath and, in some cases, over a guidewire into a position for performing a medical procedure. Thus, the introducer sheath may facilitate introducing the catheter or other intraluminal device into the vessel, while minimizing trauma to the vessel wall and/or minimizing blood loss during a procedure.

Delivery systems of the invention may optionally involve the use of an outer catheter or sheath. Outer catheters or sheaths define a lumen through which subsequent interventional/delivery micro-catheters, push rods, or wires and implantation devices are introduced into the vessel of interest. For example, the outer catheter or sheath may be used to provide a path for systems of the invention to move within the vessel to the target implantation site. Outer catheters/sheaths reduce the risk of the implant damaging the vessel or becoming dislodged while it is being driven to the implantation site by the delivery member. In certain embodiments, the outer catheter sheath can be used to delivery an electrolytic fluid into the blood vessel. In further embodiments, the outer catheter sheath may also be the pull-back sheath, which exposes the junction to an electrolytic fluid (discussed in more detail with reference to FIGS. 8A-8B).

Aspects of the invention rely on the galvanic corrosion of a junction that links an implantable device to a delivery member. Galvanic corrosion is an electrochemical process in which one metal corrodes preferentially to another when both metals are in electrical contact and immersed or exposed to an electrolyte. Galvanic corrosion generally requires two dissimilar metals, an electrolyte and a common electrical connection (for transfer of ions and electrons). Galvanic corrosion relies on the different electrode potentials of the dissimilar metals, which is the relative measure of a metal's tendency to become active in an electrolytic environment. For example, a metal that is more active (less nobel) will act as anode when in the same electrolytic environment as a less active (more nobel) metal, which will act as a cathode. When exposed to an electrolyte (i.e. electrolytic fluid), the electropotential difference between the dissimilar metals causes accelerated corrosion of the anodic metal into the electrolyte as well as its deposition on the cathodic metal. The accelerated corrosion occurs because the electrolyte acts as a conduit for metal ion migration from the anode to the cathode.

Referring now to the figures, FIG. 1 depicts generally the conditions 50 required for galvanic corrosion to occur. As shown in FIG. 1, an anodic metal 12 is in electrical contact with a cathodic metal 10 (i.e. the metals are abutting). The abutting metals 10, 12 are then exposed to an electrolytic environment 14. Typically, the electrolytic environment is a fluid with electrolytes, such as saline, or blood. When exposed to the electrolytic environment, the anodic metal 12 corrodes/dissolves (as shown by the dotted line) and the cathodic metal 10 remains.

FIG. 2 generally illustrates a system of the invention with a junction 100 that utilizes the conditions 50 as set forth in FIG. 1. As shown in FIG. 2, the system 200 includes a junction 100 that couples an implantable device 16 to a delivery member 18. The delivery member 18 may be a wire, push rod, or micro-catheter. The delivery member may be sized to fit a body lumen, such as those discussed above. Delivery members intended for intravascular introduction will typically have a length in the range from 50 cm to 200 cm and an outer diameter in the range from 1 French to 12 French (0.33 mm: 1 French), usually from 3 French to 9 French. In the case of coronary catheters, the length is typically in the range from 125 cm to 200 cm, the diameter is preferably below 8 French, more preferably below 7 French, and most preferably in the range from 2 French to 7 French. It is understood that delivery members for use in the cerebrovascular may be smaller in diameter.

In certain embodiments, the delivery member is a wire or push rod. In such instance, the wire or push rod may include a solid metal or polymer core. Suitable polymers include polyvinylchloride, polyurethanes, polyesters, polytetrafluoroethylenes (PTFE), silicone rubbers, natural rubbers, and the like. Preferably, at least a portion of the metal or polymer core and other elements that form the wire or push rod are flexible.

In certain embodiments, the delivery member is a microcatheter. Catheter bodies (including the microcatheter or outer catheter) will typically be composed of an organic polymer that is fabricated by conventional extrusion techniques. Suitable polymers include polyvinylchloride, polyurethanes, polyesters, polytetrafluoroethylenes (PTFE), silicone rubbers, natural rubbers, and the like. Optionally, the catheter body may be reinforced with braid, helical wires, coils, axial filaments, or the like, in order to increase rotational strength, column strength, toughness, pushability, and the like. Suitable catheter bodies may be formed by extrusion, with one or more channels being provided when desired. The catheter diameter can be modified by heat expansion and shrinkage using conventional techniques. The resulting catheters will thus be suitable for introduction to the vascular system, often the coronary arteries, by conventional techniques. Preferably, at least a portion of the catheter body is flexible.

Referring back to FIG. 2, the junction 100 of the delivery system 200 includes at least two dissimilar metals, at least one cathode and at least one anode. The dissimilar metals are arranged such that exposure of the junction 100 to an electrolytic environment causes the implantable device 16 to detach from the delivery member 18 due to corrosion of the anodic metal. The various configurations of the dissimilar metals of the junction 100 with respect to each other and with respect to the implant 16 and the delivery member 18 are discussed in further detail hereinafter with reference to FIGS. 4-7.

Systems of the invention are useful to delivery implants to an implantation site and easily detach the implant into the implantation site without use of an external energy source. FIGS. 3A-3C illustrate a system of the invention being used to delivery and detach an implant in to an aneurysm sac. FIG. 3A illustrates an optional outer catheter 300 disposed within a blood vessel 320 next to the target implantation site, the aneurysm sac 340. Once the optional outer catheter 300 is positioned at the aneurysm, an implant 16, shown as an embolic coil, is deployed from the outer catheter 300 into the aneurysm sac 340. A delivery member 18 is used to deploy the coil 16, which is attached to delivery member 18 at the junction 18. The junction 100 is formed from at least one anodic metal and at least one cathodic material. The coil 16 is continually pushed into the sac 340 by the delivery member 18 causing it curl/fold over itself within the sac 340, thereby forming an occlusion in the sac 340. As further shown in FIG. 3B, an electrolytic fluid 14 is used to galvanically corrode the junction 18. The electrolytic fluid 14 may be present during the deployment of the implant or may be introduced into the vessel after deployment of the implant. In certain embodiments, blood or other body fluids are present during deployment of the implant. In certain embodiments, saline solution or other biocompatible fluids are introduced into the vessel during and/or after deployment of the implant. While in the presence of the electrolytic fluid 14, the anodic metal of the junction 100 undergoes accelerated corrosion without application of an external energy source, thereby detaching the implant 16 from the delivery member 18 (as shown in FIG. 3C). The delivery member 18 and outer catheter 300 may then be removed from the blood vessel 320 and the implant 16 is left deposited in the aneurysm sac 340. While the method depicted in FIGS. 3A-3C is directed to a coil implant for occlusion of an aneurysm, it is understood that the same principles and steps can be used to delivery and detach other implants for other treatment purposes.

FIGS. 4-7 illustrate different configurations of the dissimilar metals that form the junction 100 according to aspects of the invention. As shown in FIGS. 4-7, segments of the cathodic and anodic portions 10, 12 are at least partially exposed so that the dissimilar metals can come in contact with an electrolytic fluid. In the various configurations, the cathodic portion(s) 10, anodic portion(s) 12, proximal portion 58 of implant 16, or distal portion 56 of the delivery member 18 may be coupled to each other by bonding techniques known in art (e.g. mechanical, adhesive) and using any suitable joint, including butt joints, overlapping joints, and lap joints. In certain embodiments, a mechanical band (such as a radiopaque band) is used to couple the junction 100 to the implant 16 or delivery member 18. In other embodiments, the junction 100 can be coupled to the implant 16 or delivery member 18 via hooks, tabs, etc. Throughout the configurations depicted in FIGS. 4-7, the cathodic and anodic portions 10, 12 are preferably cylindrical in nature, but may be other shapes. Additionally, the cross-sections of the anodic portion(s) 12 and cathodic portion(s) 10 may vary across their lengths. For configurations with two or more cathodic or anodic portions, the multiple cathodic or anodic portions may be the same size or different size (e.g., vary in cross-section and/or length) and may be the same metal or different metal (e.g., cathodic portions-vary in level of inactiveness and anodic portions-vary in level of activeness). In addition, it is understood that positions of the cathodic portion(s) and the anodic portion(s) shown in FIGS. 4-7 can be swapped or interchanged.

Figure 4:
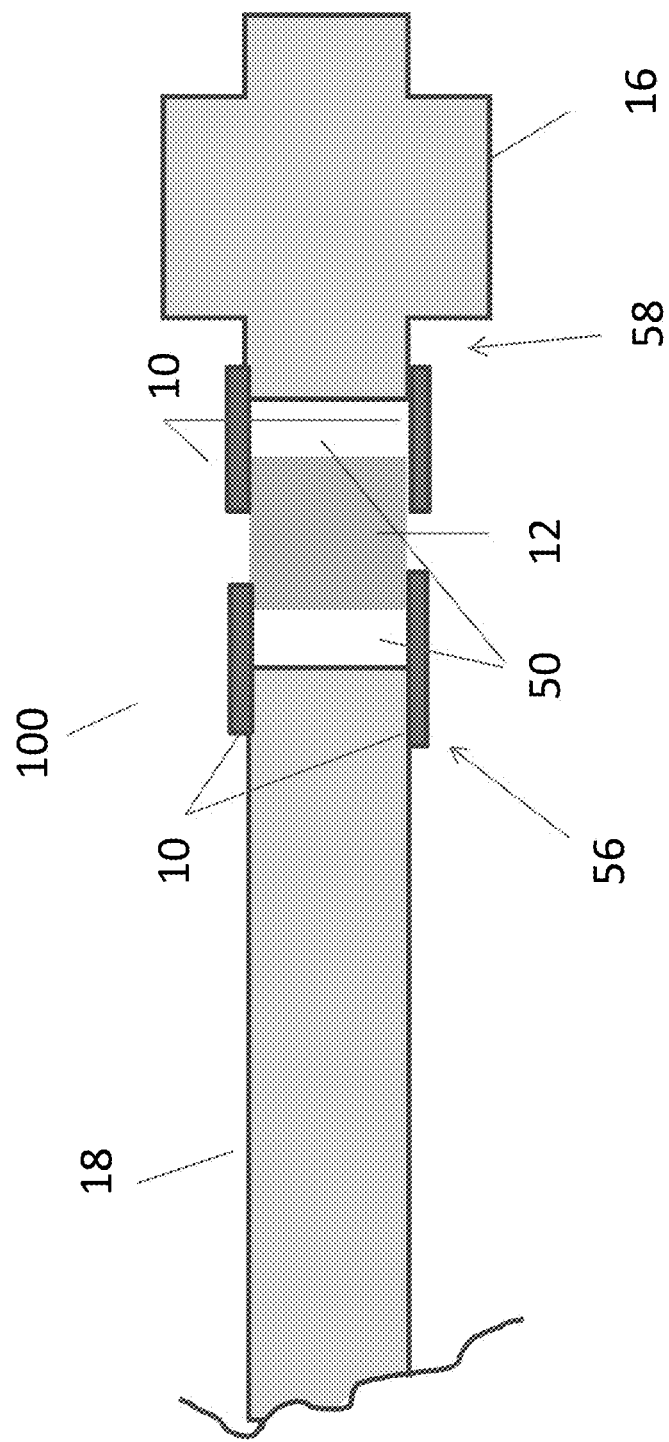
FIG. 4 illustrates a hollow/rod/hollow configuration of the junction.
Figure 5:
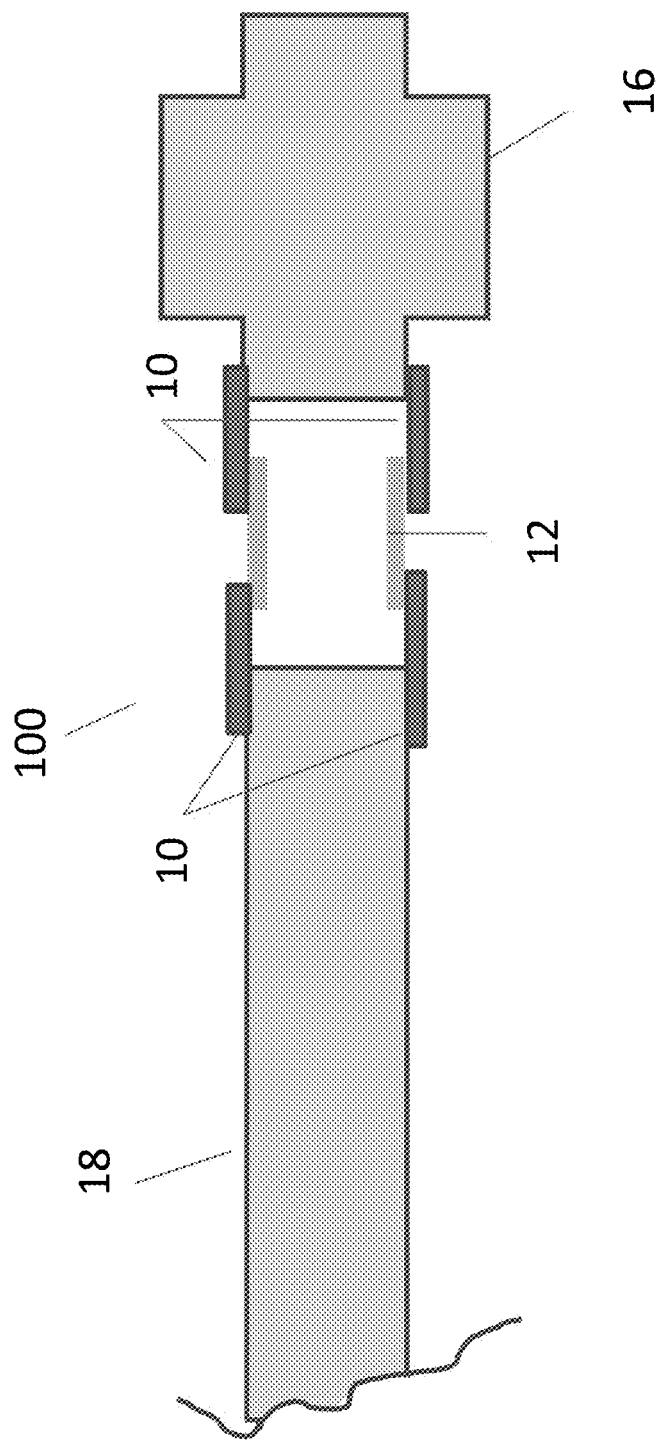
FIG. 5 illustrates a hollow/hollow/hollow configuration of the junction.

FIGS. 4 and 5 illustrate cross-sections of delivery systems that include sandwich junctions, in which at least one metal (typically the anodic portion) is exposed and sandwiched between two or more dissimilar metals (typically the cathodic portion). FIG. 4 illustrates a cross-section of the delivery system showing a hollow/rod/hollow configuration of the junction 100. As shown in FIG. 4, the junction 100 includes at least two cathodic portions 10 (i.e. inactive metal or alloy) and at least one anodic portion 12 (active metal or alloy). In the hollow/rod configuration, the cathodic portions 10 are hollow structures (e.g. a tube) that define lumen and the anodic portion 12 is a solid rod (or vice versa). In FIG. 4, the cathodic portions 10 are coupled to the anodic portion 12, implant 16 and delivery portion 18 via an overlapping joint in which the cathodic portions 10 are the outer-overlapping member. It is understood that the cathodic portion(s) 10 may also be the inner-overlapping member, e.g., if the implant 16 or delivery member 18 define a lumen with a cross-section greater than the cathodic portion(s). FIG. 5 illustrates a hollow/hollow/hollow configuration, which is similar to that shown in FIG. 4, except that the anodic portion 12 is also a hollow structure (e.g. tube) that defines a lumen.

Figure 6:
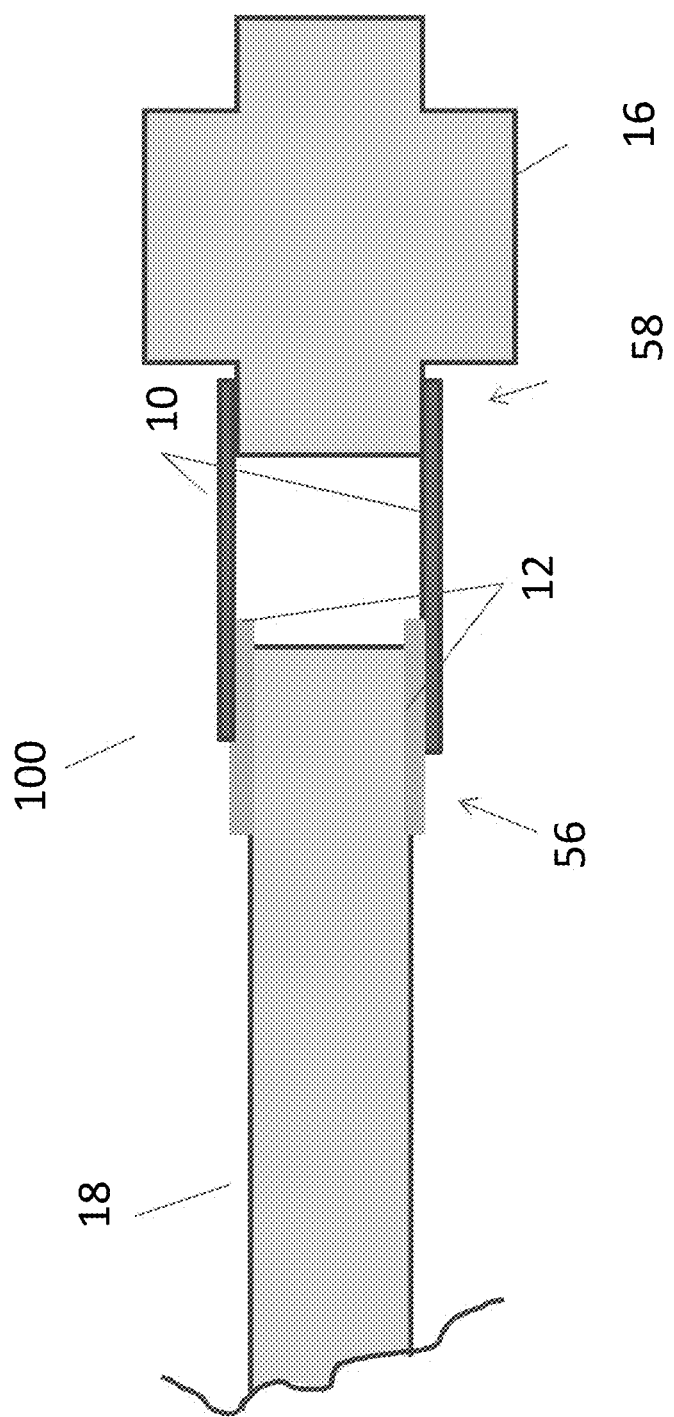
FIGS. 6 and 7 illustrate cross-sections of delivery systems of the invention that include direct junction configurations.
Figure 7:
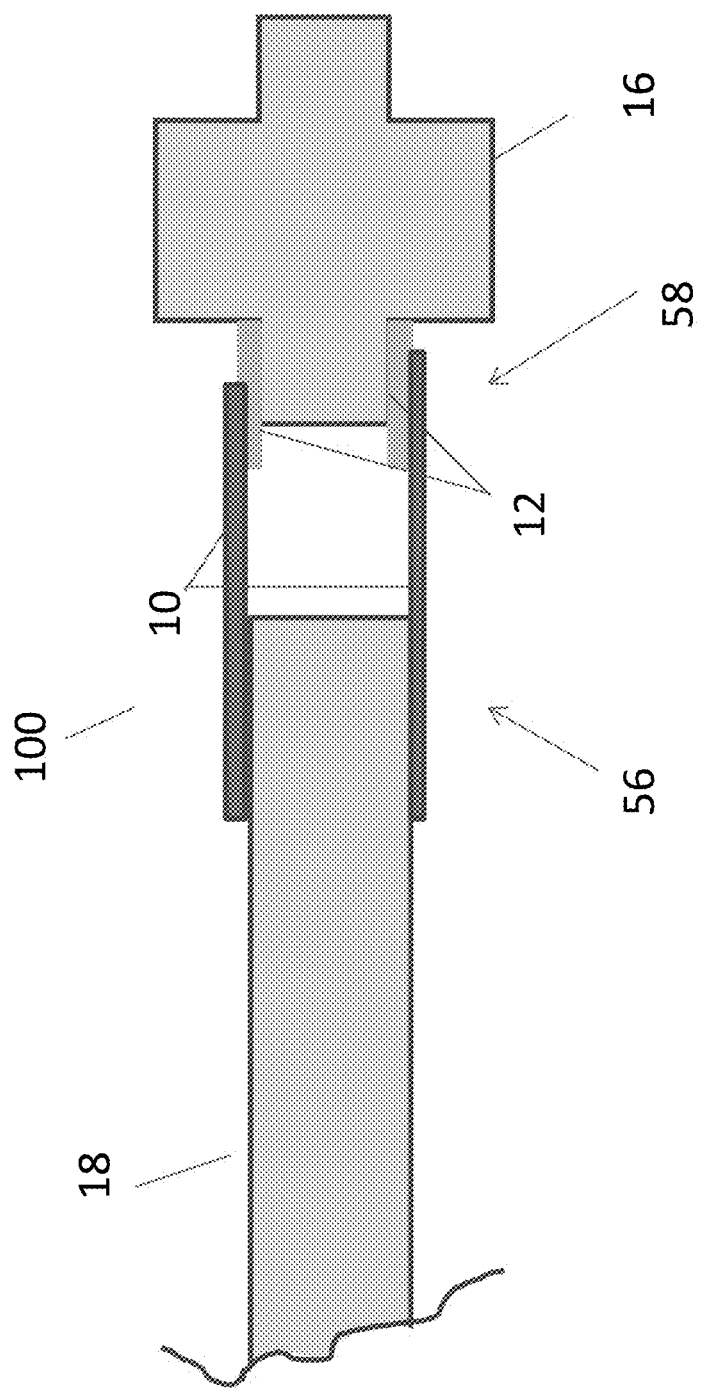

FIGS. 6 and 7 illustrate cross-sections of delivery systems that include direct junctions. Direct junctions include at least one metal extending (bridging) from the delivery member 18 to the implant 16 and at least one other metal being operably associated with a distal portion of the delivery member 18, a proximal portion of the implant 16 or both. As exemplified in FIG. 6, an anodic metal 12 is operably associated with the distal portion 56 of the delivery member 18, and the cathodic metal 10 extends from the proximal portion 58 of the implant 16 to the distal portion 56 of the delivery member 18. As exemplified in FIG. 7, the anodic metal 12 is operably associated with the proximal portion 58 of the implant 16, and the cathodic metal 10 extends from the proximal portion 58 of the implant 16 to the distal portion 56 of the delivery member 18. The anodic metal 12 may be, for example, a tubular member coupled to or a thin film/layer deposited onto the implant 16 or delivery member 18. The thin film or layer of the anodic metal 12 may be deposited or formed on the delivery member 18 or implant 16 using any known techniques, such as dipping, physical deposition, chemical deposition, laser deposition/sputtering, plating, etc. The cathodic metal 10 is typically a hollow structure, such as a tube, that forms an overlapping joint with the delivery portion 18, implant 16, and the anodic material 12 formed on either.

According to certain embodiments, the materials/features of the junction 100 (e.g., as shown in FIGS. 4-7) as well as the electrolytic conditions can be chosen to achieve rapid or controlled corrosion of the junction for detaching the implant 16 from the delivery device 18. These features and conditions include, for example, the type of metals forming the junction, dimensions/shape of the metals forming the junction, the surface area ratio of the metals forming the junction, presence of surface modifications, the type of electrolytic fluid, the flow rate of the electrolytic fluid, and temperature of the electrolytic environment. These features and conditions can be used alone or in combination with any junction configuration (e.g. as shown in FIG. 4-7) to achieve ideal dissolution (i.e. preferred level of corrosion and level of corrosion). In certain embodiments, the ideal dissolution time after the junction is exposed to the electrolytic fluid ranges from seconds to minutes. For example, rapid dissolution may be achieved in less than 4 seconds. The dissolution time can be in the range from 2 seconds to 2 hours, preferably between 2 seconds and 30 minutes.

These features and conditions are discussed in more detail below, and can be used alone or in combination to achieve ideal dissolution of a junction of the invention (including the configurations illustrated in FIGS. 4-7).

The type of dissimilar metals chosen for cathodic portion and anodic portion directly affects corrosion rate. When two dissimilar metals or alloys join together in an electrolyte form a galvanic couple. When exposed to the electrolyte, the metals each have their own electric potential. Nobel metals (cathodic) having greater potentials than active metals (anodic). Generally, the greater difference between the potentials of the cathodic metal and the active metal, the greater the galvanic corrosion. The following is a galvanic table for metals in seawater environment. For any combination of dissimilar metals, the metal with the lower number will act as the anode and will corrode preferentially to metals listed at a higher number on the table.

| Level of Activity (Starting with most Active) | Metal or Metal Alloy |
|---|---|
| 1. | Magnesium |
| 2. | Mg alloy AZ-31B |
| 3. | Mg alloy HK-31A |
| 4. | Zinc (hot-dip, die cast, or plated) |
| 5. | Beryllium (hot pressed) |
| 6. | Al 7072 clad on 7075 |
| 7. | Al 2014-T3 |
| 8. | Al 1160-H14 |
| 9. | Al 7079-T6 |
| 10. | Cadmium (plated) |
| 11. | Uranium |
| 12. | Al 218 (die cast) |
| 13. | Al 5052-0 |
| 14. | Al 5052-H12 |
| 15. | Al 5456-0, H353 |
| 16. | Al 5052-H32 |
| 17. | Al 1100-0 |
| 18. | Al 3003-H25 |
| 19. | Al 6061-T6 |
| 20. | Al A360 (die cast) |
| 21. | Al 7075-T6 |
| 22. | Al 6061-0 |
| 23. | Indium |
| 24. | Al 2014-0 |
| 25. | Al 2024-T4 |
| 26. | Al 5052-H16 |
| 27. | Tin (plated) |
| 28. | Stainless steel 430 (active) |
| 29. | Lead |
| 30. | Steel 1010 |
| 31. | Iron (cast) |
| 32. | Stainless steel 410 (active) |
| 33. | Copper (plated, cast, or wrought) |
| 34. | Nickel (plated) |
| 35. | Chromium (Plated) |
| 36. | Tantalum |
| 37. | AM350 (active) |
| 38. | Stainless steel 310 (active) |
| 39. | Stainless steel 301 (active) |
| 40. | Stainless steel 304 (active) |
| 41. | Stainless steel 430 (active) |
| 42. | Stainless steel 410 (active) |
| 43. | Stainless steel 17-7PH (active) |
| 44. | Tungsten |
| 45. | Niobium (columbium) 1% Zr |
| 46. | Brass, Yellow, 268 |
| 47. | Uranium 8% Mo. |
| 48. | Brass, Naval, 464 |
| 49. | Yellow Brass |
| 50. | Muntz Metal 280 |
| 51. | Brass (plated) |
| 52. | Nickel-silver (18% Ni) |
| 53. | Stainless steel 316L (active) |

-continued

| Level of Activity (Starting with most Active) | Metal or Metal Alloy |
|---|---|
| 54. | Bronze 220 |
| 55. | Copper 110 |
| 56. | Red Brass |
| 57. | Stainless steel 347 (active) |
| 58. | Molybdenum, Commercial pure |
| 59. | Copper-nickel 715 |
| 60. | Admiralty brass |
| 61. | Stainless steel 202 (active) |
| 62. | Bronze, Phosphor 534 (B—I) |
| 63. | Monel 400 |
| 64. | Stainless steel 201 (active) |
| 65. | Carpenter 20 (active) |
| 66. | Stainless steel 321 (active) |
| 67. | Stainless steel 316 (active) |
| 68. | Stainless steel 309 (active) |
| 69. | Stainless steel 17-7PH (passive) |
| 70. | Silicone Bronze 655 |
| 71. | Stainless steel 304 (passive) |
| 72. | Stainless steel 301 (passive) |
| 73. | Stainless steel 321 (passive) |
| 74. | Stainless steel 201 (passive) |
| 75. | Stainless steel 286 (passive) |
| 76. | Stainless steel 316L (passive) |
| 77. | AM355 (active) |
| 78. | Stainless steel 202 (passive) |
| 79. | Carpenter 20 (passive) |
| 80. | AM355 (passive) |
| 81. | A286 (passive) |
| 82. | Titanium 5A1, 2.5 Sn |
| 83. | Titanium 13V, 1 ICr, 3A1 (annealed) |
| 84. | Titanium 6A1, 4V (solution treated and aged) |
| 85. | Titanium 6A1, 4V (anneal) |
| 86. | Titanium 8Mn |
| 87. | Titanium 13V, 1 ICr 3Al (solution heat treated and aged) |
| 88. | Titanium 75A |
| 89. | AM350 (passive) |
| 90. | Silver |
| 91. | Gold |
| 92. | Graphite |

The above galvanic table list metals in the order of their relative activity in a sea water environment. The list beings with the more active, anodic metal (lower number) and progresses to the least active, cathodic metals. According to certain embodiments, the dissimilar metals of the junction are chosen based on their galvanic activity levels relative to each other. For example, the closer the anodic portion and the cathodic portion are to each other in terms of galvanic activity, the slower the galvanic corrosion of the anodic portion. Likewise, the further away the anodic portion is from the cathodic portion in terms of galvanic activity, the faster the galvanic corrosion of the anodic portion. According to certain embodiments, the anodic portion of the junction is formed from magnesium and magnesium alloys; and the cathodic portion of the junction is formed platinum, platinum alloys, platinum-iridium alloys, tantalum, stainless steel, nickel-titanium alloys, cobalt-chromium alloys, or combinations thereof.

According to further embodiments, the dimensions of the metals forming the junction are chosen to increase or decrease the length of the detachment event. For example, the thicker the anodic portion, the longer it will take for the anodic portion to dissolve from the galvanic reaction. Generally, the detachment event will occur sooner when there is less anodic portion to erode. When a quicker detachment event is desirable, the anodic portion chosen for the junction may be a thin film or layer. In certain embodiments, the metal forming the anodic portion is a woven or perforated to reduce the amount of erosion that needs to occur for attachment. When a longer detach detachment event is desirable, the amount of metal forming the anodic portion is increased in size (e.g. thickness).

Similarly and related to the dimensions, the surface area ratio of the anodic portion to the cathodic portion affects the rate of the detachment event. According to certain embodiments, the surface area of the anodic portion is smaller than the surface area of the cathodic portion of the junction. In such embodiments, the surface area ratio of the anodic material to the cathodic material can be in the range of 0.0001% to 50%. The smaller the surface area of the anodic portion compared to the surface area of the cathodic portion, the greater the detachment event because there higher current density in the smaller anodic material. In additional embodiments, the surface area of the anodic portion is larger than the surface area of the cathodic portion of the junction. In such embodiments, the surface area ratio of the cathodic material to the anodic material can be in the range of 0.0001% to 50%. When the surface area of the anodic portion is greater than the surface area of the cathodic portion, the detachment time is increased.

In further embodiments, the cathodic portion, anodic portion, or both have surface modifications to affect corrosion rate. Surface modification that facilitate corrosion include, for example, a surface roughening treatment; a thin, sparse or lack of an oxidation layer; an acid activated surface; and a cold worked layer. Surface modifications that inhibit or slow corrosion include, for example, a passivation treatment and thick or uniform oxidation layer. Depending on the desired corrosion rate, the anodic portion, cathodic portion, or both may be subject to the above surface modifications. In certain embodiments, the anodic portion of a junction is subjected to surface modifications to promote dissolution and the cathodic portion of the junction is subjected to surface modifications to promote corrosion resistance.

As discussed above, galvanic corrosion of the junction requires exposure to an electrolyte or fluid containing electrolytes. Typically, the corrosion rate increases as the concentration of electrolytes increases. Common electrolytes suitable for use in accordance with the invention include sodium, potassium, chloride, and bicarbonate, all of which are present in one's blood. In certain embodiments, the electrolytic fluid is a biological fluid, such as blood or plasma. In other embodiments, the electrolytic fluid is a non-biological fluid, such as saline solution.

The blood electrolytic environment is ideal because it's a natural environment of the patient. Normal blood has a sodium concentration between 135 and 145 milliequivalents per liter (mEq/L) of sodium. When a higher corrosion rate or lower corrosion rate than that achievable with blood, a non-biological electrolytic fluid may be introduced into the body lumen to effectuate galvanic corrosion. In certain embodiments, the non-biological electrolytic fluid is saline solution. The saline solution may have a salt concentration ranging from 0.1%, 0.2%, 0.3%, 0.4%, 0.5%, 0.6%, 0.7%, 0.8%, 0.9%, 1.0%, 1.1% . . . 3.8%, 3.9%, 4.0%. A saline concentration of 0.9% contains about 154 mEq/L of sodium. A saline solution with a sodium concentration greater than blood may be introduced to increase the corrosion rate that is achievable with blood. A saline solution with a sodium concentration less than blood may be introduced to decrease the corrosion rate that is achievable with blood.

In addition to the type of electrolytic fluid, the flow rate and the temperature of electrolytic environment also affects detachment rates. Higher flow rates increase the rate of the corrosion event as well as higher temperatures. In certain embodiments, the flow rate of an electrolytic fluid introduced into the body lumen is chosen to increase or decrease detachment times. In other embodiments, the temperature of an electrolytic fluid introduced into the body lumen is chosen to increase or decrease detachment times. In further embodiments, both the temperature and the flow rate are chosen to increase or decrease the detachment times.

In some embodiments, the initiation of and rate of the galvanic corrosion event is controlled by inhibiting or delaying exposure of the junction to the electrolytic fluid. For example, an operator may not want the galvanic corrosion event to begin until after the implant is fully deployed and properly positioned. Alternatively, an operator, knowing galvanic corrosion may take several minutes, may want to initiate galvanic corrosion during implant deployment. Any technique for delaying or inhibiting exposure of the junction to the electrolytic fluid may be utilized. Exemplary techniques include using a pull-back sheath, placing a permeable/perforated sheath over the junction, or applying a coating/sheath over the junction that will dissolve over time. The dissolvable coating or sheath may be formed from any biocompatible and biodegradable material, such as a polymeric material. For example, the coating may be a soluble glue (e.g., blood or saline soluble) or a salt layer.

FIGS. 8A and 8B illustrate use of a pull-back sheath to delay exposure of the junction to an electrolytic fluid. As shown in FIG. 8A, the delivery member 18 is disposed within a pull-back sheath 20. When corrosion is not desired, the pull-back sheath 18 is positioned over the junction 100. The pull-back sheath 20 may remain in the position shown in FIG. 8A, for example, while the delivery member 18 moves within the body lumen to the target implantation and during placement of the implant 16. Once corrosion is desired, the pull-back sheath 20 may be pulled-back, as shown by the arrow in FIG. 8B, to expose the junction 100 to an electrolytic fluid, thereby initiation corrosion.

Figure 9:
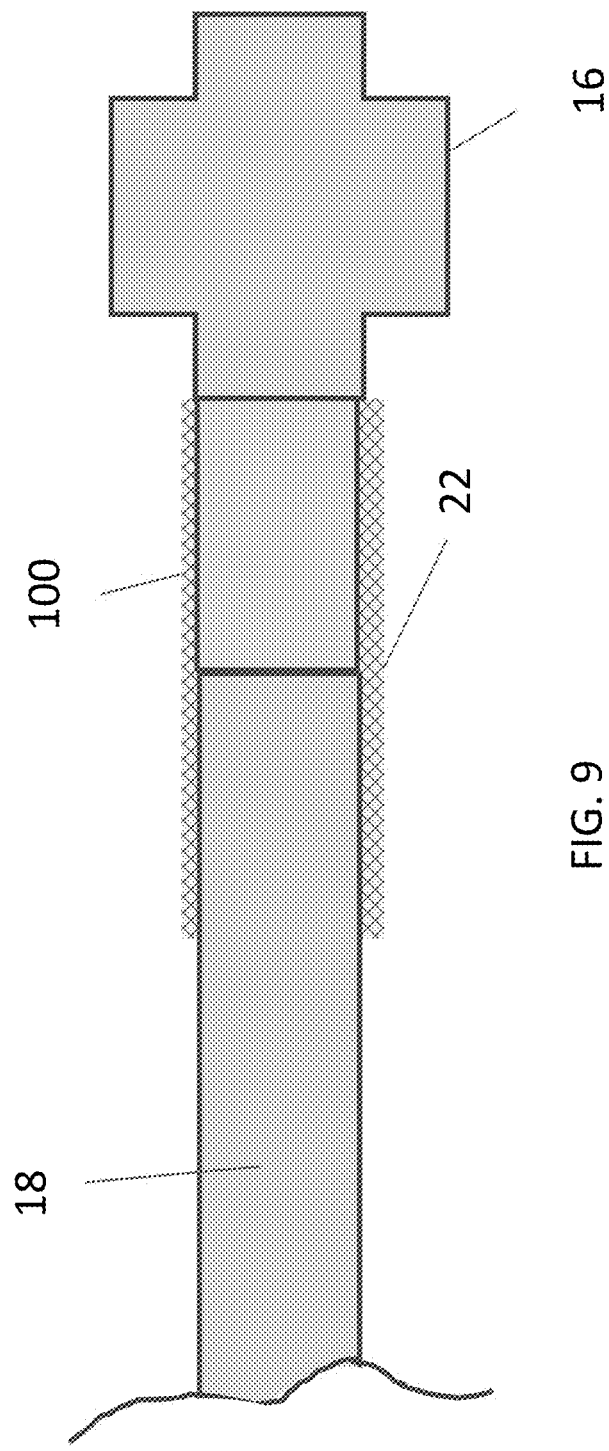
FIG. 9 illustrates a permeable/perforated membrane for hindering exposure of the junction to an electrolytic fluid.

FIG. 9 illustrates a permeable/perforated membrane, according to certain embodiments. As shown in FIG. 9, a permeable membrane 22 is positioned over the junction 100 and at least partially over the delivery member 18. The permeable membrane 22 reduces the rate at which electrolytic fluid contacts the junction 100. The less porous the membrane, the slower the exposure rate (and thus galvanic corrosion rate). In certain embodiments, the membrane 22 is a woven polymer, although other biocompatible materials are suitable for use.

The delivery member, implant, or elements coupling the junction to the delivery member and/or implant may include one or more radiopaque markers. The radiopaque markers allow one to determine the positioning of the catheter relative to the vasculature when viewed with an external imaging modality (such as fluoroscopy). This further aids in determining whether the catheter is appropriately placed for implantation of, e.g., a vaso-occlusion device.

Figure 10:
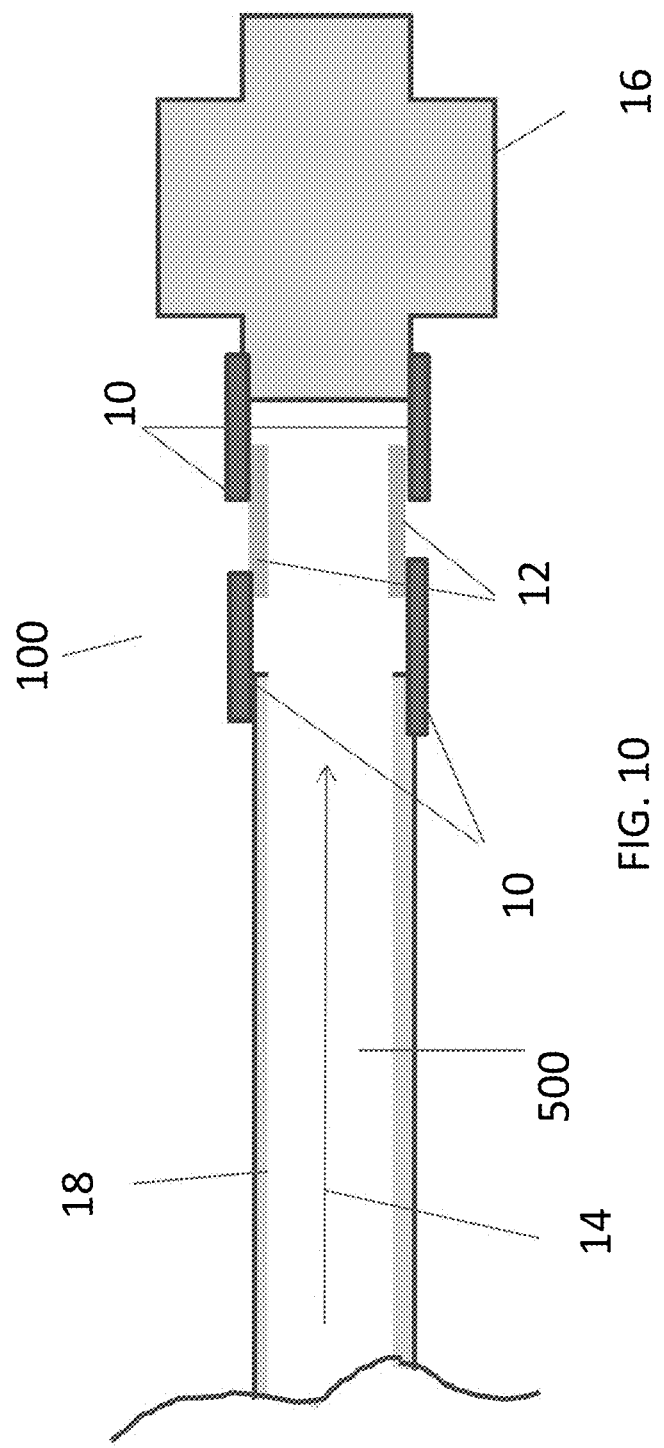
FIG. 10 depicts an embodiment of the delivery member that includes a lumen for fluid delivery.

As discussed previously, the electrolytic fluid may be blood, plasma, or a non-biological solution. In certain embodiments, the electrolytic fluid may be introduced into a body lumen (e.g., blood vessel) from one or more external fluid sources (external source of blood, plasma, or saline solution, e.g.). In one embodiment, the electrolytic fluid may be introduced into, e.g., a blood vessel through a lumen of an outer catheter sheath, in which a system of the invention is also deployed therethrough. In another embodiment, the electrolytic fluid may be introduced into the blood vessel through a separate fluid delivery catheter. In yet another embodiment and as shown in FIG. 10, the delivery member 18 may define a lumen 500 through which electrolytic fluid 14 may be introduced.

Generally, delivery systems of the invention include a junction coupling an implant to a delivery member. Systems of the invention can be introduced into and driven through a body lumen to a target implantation site. At the target implantation site, the implant may be positioned and detached. Systems of the invention utilize a junction that can be corroded galvanically without application of an external power source. The junction is formed from an anodic portion galvanically coupled to a cathodic portion such that the anodic portion corrodes when in the presence of an electrolytic fluid. Corrosion of the anodic portion detaches the implant, and allows removal of the delivery member from the body lumen.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A system for delivering an implantable device into a body lumen, the system comprising:
    an implantable device;
    a delivery member having first and second ends; and
    a junction coupling the implantable device to the delivery member, the junction comprising:
        a tubular anodic portion surrounding a portion of the first end of the delivery member; and
        a tubular cathodic portion having opposing first and second ends, with the first end overlapping a portion of the anodic portion and a portion of the first end of the delivery member without directly contacting the delivery member, in a manner such that the anodic portion extends beyond the first end of the delivery member, and the second end of the cathodic portion overlapping a portion of the implantable device.

2. The system of claim 1, wherein the anodic portion corrodes when exposed to an electrolytic fluid, thereby detaching the implantable device from the delivery member without application of energy from an external power source.

3. The system of claim 2, wherein the electrolytic fluid is selected from the group consisting of blood, saline, and a combination thereof.

4. The system of claim 1, wherein the anodic portion is formed on and overlaps a distal end of the delivery member, and the first end of the cathodic portion overlaps a proximal end of the implantable device.

5. The system of claim 1, wherein the anodic portion is formed on the delivery member by dipping, physical deposition, chemical deposition, laser deposition/sputtering, or plating.

6. The system of claim 1, wherein the cathodic portion comprises a material selected from the group consisting of platinum, platinum alloys, platinum-iridium alloys, tantalum, stainless steel, nickel-titanium alloys, and cobalt-chromium alloys.

7. The system of claim 1, wherein the anodic portion comprises a material selected from the group consisting of magnesium and magnesium alloys.

* * * * *